United States Patent [19]
Thiele et al.

[11] Patent Number: 5,767,308
[45] Date of Patent: Jun. 16, 1998

[54] PERCARBOXYLIC ACID SOLUTIONS WITH IMPROVED STABILITY WHEN IN CONTACT WITH STAINLESS STEEL AND PROCESS FOR PRODUCING SAID PERCARBOXYLIC ACID SOLUTIONS

[75] Inventors: Georg Thiele, Hanau, Germany; Peter Taeubl, Weissenstein, Austria

[73] Assignee: Degussa Aktiengesellschaft, Frankfurt, Germany

[21] Appl. No.: 646,395

[22] Filed: May 8, 1996

[30] Foreign Application Priority Data

May 12, 1995 [DE] Germany ............... 195 17 465.8

[51] Int. Cl.⁶ .................. C07C 407/00; C07C 409/24
[52] U.S. Cl. ........................................................... 562/3
[58] Field of Search .................................................. 162/3

[56] References Cited

U.S. PATENT DOCUMENTS

| | | |
|---|---|---|
| 2,347,434 | 4/1944 | Reichert et al. |
| 3,122,417 | 2/1964 | Blaser ................................ 562/3 |
| 3,168,554 | 2/1965 | Phillips et al. |
| 3,442,937 | 5/1969 | Sennewald et al. |

FOREIGN PATENT DOCUMENTS

| | | |
|---|---|---|
| 0626371 | 11/1994 | European Pat. Off. |
| 43 17 429 | 11/1994 | Germany. |
| 4243861 | 8/1992 | Japan. |

Primary Examiner—Paul J. Killos
Attorney, Agent, or Firm—Beveridge, DeGrandi, Weilacher & Young, LLP.

[57] ABSTRACT

Percarboxylic acid solutions, in particular aqueous equilibrium percarboxylic acid solutions, with improved stability when in contact with stainless steel and also a process for the production thereof. The percarboxylic acid solutions contain a percarboxylic acid having 1 to 12 C atoms and one or two peroxycarboxyl groups and are characterized by a content of polyphosphoric acid of the formula $H_{n+2}P_nO_{3n+1}$, in which n is greater than or equal to 2.3, in a quantity of 0.2 to 10 wt. %. These solutions are distinguished in comparison with known solutions by reduced corrosive action and reduced decomposition in the presence of stainless steel. The solutions are obtainable by reacting a carboxylic acid with hydrogen peroxide in the presence of polyphosphoric acid of the above-stated type and quantity as the catalyst.

19 Claims, No Drawings

PERCARBOXYLIC ACID SOLUTIONS WITH IMPROVED STABILITY WHEN IN CONTACT WITH STAINLESS STEEL AND PROCESS FOR PRODUCING SAID PERCARBOXYLIC ACID SOLUTIONS

INTRODUCTION AND BACKGROUND

The present invention relates to percarboxylic acid solution with improved stability when in contact with stainless steel and to a process for the production thereof. The percarboxylic acid solutions are organic solutions, preferably however aqueous solutions, in particular so-called equilibrium percarboxylic acid solutions, wherein the percarboxylic acid has 1 to 12 C atoms and one or two peroxycarboxyl groups.

Percarboxylic acid solutions, in particular aqueous solutions, which contain a water soluble lower percarboxylic acid, have many uses, for example in detergents, bleaches and cleaning products, as well as in microbicidally active compositions for disinfection purposes in the industrial or also domestic sectors. Percarboxylic acid solutions in low-water or anhydrous organic solvents are used as oxidizing agents in chemical synthesis.

In order to produce a percarboxylic acid solution, the carboxylic acid is reacted in the presence or absence of an organic solvent with hydrogen peroxide, conventionally using an aqueous hydrogen peroxide solution, in the presence of a strongly acidic catalyst. Unless the equilibrium is affected by external measures, for example by azeotropic removal of water, the reaction proceeds until an equilibrium is established, and the resultant reaction mixture is termed an equilibrium percarboxylic acid solution. Such an equilibrium percarboxylic acid solution thus contains, in addition to the percarboxylic acid, a solvent system, which is taken to mean the unreacted carboxylic acid, water (from the aqueous hydrogen peroxide, water of reaction, optionally together with added water) together with unreacted hydrogen peroxide and, if present, water soluble organic solvents. The time required to reach equilibrium depends upon the quantity and acid strength of the added catalyst; sulfuric acid or nitric acid are thus in practice conventionally used as the catalyst.

Due to the fire and explosion hazard which they present, lower percarboxylic acids are most frequently handled as solutions; however, even in such solutions, decomposition phenomena occur at elevated temperature, elevated pH and in particular in the presence of catalytically active heavy metal ions, thereby bringing about a reduction in the percarboxylic acid content. Since factors which impair stability cannot ever in practice be excluded during production, storage and handling of percarboxylic acid solutions, one or more stabilizers, preferably synergistically active combinations, are added during and/or after the production thereof, conventionally in a quantity of below 0.1 wt. % relative to the solution. Known stabilizers are, for example, dipicolinic acid (U.S. Pat. No. 2,609,391 which is incorporated by reference in its entirety), pyrophosphate or pyrophosphoric acid (U.S. Pat. No. 2,347,434 which is incorporated by reference in its entirety), together with a combination of the two stated classes of substances (DE 43 17 420). According to U.S. Pat. No. 2,590,856 (which is incorporated by reference in its entirety), dilute aqueous percarboxylic acid solutions may be stabilized by the addition of 100 to 1000 ppm of a polymeric phosphate with a molar ratio of $R_2O$ to $P_2O_5$ of no greater than 1.7 to 1, wherein R represents alkali metal, ammonium or hydrogen.

Percarboxylic acid solutions exhibit an unwanted corrosive action towards many metallic materials, especially stainless steel, which, in addition to damaging the metallic material, also dissolves metal ions from the metallic material, thereby contaminating the percarboxylic acid solution. The decomposition of the percarboxylic acid catalyzed by these metal ions cannot be prevented by the usual stabilizers and the liberated heat may additionally give rise to a dangerous, self-accelerating decomposition reaction. The storage and transport of percarboxylic acid solutions, in particular aqueous percarboxylic acid solutions, in stainless steel containers thus gives rise to an increased safety risk, for which reason plastic containers have hitherto virtually exclusively been used for this purpose.

It is known from U.S. Pat. No. 3,890,165 (which is incorporated by reference in its entirety), that metal surfaces which come into contact with peroxy compounds, such as peracetic acid solutions, may be passivated by treatment with a polyphosphoric acid solution. Such passivation is, however, inadequate for long-term storage, in particular with a relatively large material throughput, without bringing about an increase in the tendency towards decomposition.

According to E. Muecke (*Pharmazie* (1979), 34: 573), a 0.2 wt. % aqueous peracetic acid solution in contact with iron may be stabilized for a period of one day by the addition of 1 wt. % of $Na_2H_2P_2O_7$, or of 1 wt. % of a mixture of equal parts of $Na_2H_2P_2O_7$ and $NaH_2PO_4$. According to V. B. Rudak et al. (*Zh. Prikl. Khim.* (Leningrad) (1983), 55: 2128–2130), the decomposition of an acetonic peracetic acid solution brought about by contact with stainless steel may be reduced for a period of 7 days at 20° C. by the addition of 1 wt. % of sodium pyrophosphate. JP-A 04 243 861 refers to the reduced corrosive action of peracetic acid solutions on iron by the addition of pyrophosphoric acid. Although the above-stated substances were indeed able to reduce the decomposition of percarboxylic acid solutions in the presence of stainless steel, this stabilization is inadequate for practical purposes.

SUMMARY OF THE INVENTION

An object of the present invention is to provide percarboxylic acid solutions which are distinguished by a distinctly reduced corrosive action on stainless steel and thus also by decreased decomposition. A further object of the invention is the provision of a process for the production of such percarboxylic acid solutions which is substantially equivalent to known processes with regard to its economic viability.

In achieving the above and other objects, one feature of the present invention resides in a percarboxylic acid solution with improved stability when in contact with stainless steel which contains a percarboxylic acid having 1 to 12 C atoms and one or two peroxycarboxyl groups and a solvent system, which solution is characterized by a content of a polyphosphoric acid of the formula $H_{n+2}P_nO_{3n+1}$, in which n denotes the average degree of condensation and which is greater than or equal to 2.3, in a quantity of 0.2 to 10 wt. % relative to the percarboxylic acid solution.

Another feature of the present invention is a method of producing the percarboxylic acid solution with improved stability involving reacting a carboxylic acid having 1 to 12 C atoms and one or two carboxyl groups with hydrogen peroxide in the presence of a solvent system and an acidic catalyst at a temperature 0° to 70° C. to produce a reaction mixture containing said percarboxylic acid. The catalyst is a polyphosphoric acid of the formula $H_{n+2}P_nO_{3n+1}$, in which n denotes the average degree of condensation and is greater than or equal to 2.3, in a quantity of 0.2 to 10 wt. % relative to the percarboxylic acid solution.

DETAILED DESCRIPTION OF THE INVENTION

The content, according to the present invention, of polyphosphoric acid may be added during the production of the percarboxylic acid solutions or after the production thereof. Is will be demonstrated below, the polyphosphoric acid content preferably arises from the production process; the polyphosphoric acid has in fact proved to be a highly active catalyst for the formation of a percarboxylic acid from a carboxylic acid and hydrogen peroxide. The percarboxylic acid solutions according to the present invention may contain one or more polyphosphoric acids. Since polyphosphoric acid is obtained by introducing phosphorus pentoxide into phosphoric acid, two or more polyphosphoric acids having different degrees of condensation are usually simultaneously present (see Gmelins Handbuch der anorganischen Chemie, 8th edition (1965), volume 16 P[C] 217–219 and 252–253). Preferred percarboxylic acid solutions contain polyphosphoric acid having an average degree of condensation of above three, in particular of above four. The percarboxylic acid solutions preferably contain 0.5 to 5 wt. %, in particular 1 to 3 wt. % of polyphosphoric acid.

Percarboxylic acid solutions according to the invention may contain one or more aliphatic or aromatic percarboxylic acids, which have one or two peroxycarboxyl groups; preferred solutions contain an aliphatic monoperoxycarboxylic acid having 1 to 6 C atoms, in particular peracetic acid and perpropionic acid, or an $\alpha,\omega$-diperoxydicarboxylic acid having 4 to 6 C atoms, namely diperoxysuccinic acid, diperoxyglutaric acid and diperoxyadipic acid, wherein the particular $\alpha,\omega$-diperoxydicarboxylic acid is conventionally present as a mixture with the monoperoxy-$\alpha,\omega$-dicarboxylic acid with the same number of C atoms. Preferred percarboxylic acid solutions are aqueous systems, in particular so-called equilibrium percarboxylic acid solutions. The percarboxylic acid of such aqueous solutions and the carboxylic acid on which it is based must accordingly be sufficiently water soluble; this is the case for the above-stated mono- and diperoxycarboxylic acids having up to 6 C atoms. Aqueous solutions with longer-chain percarboxylic acids additionally contain a sufficiently oxidation-resistant water soluble organic solvent as a solubilizing agent. Percarboxylic acid solutions according to the invention may also have a low water content or be substantially anhydrous, such solutions contain one or more organic solvents as the solvent, such as in particular aromatic hydrocarbons and carboxylic acid esters; such solutions may also contain mono- and diperoxycarboxylic acids having up to 12 C atoms. The solvent system of aqueous percarboxylic acid solutions accordingly substantially contains unreacted water soluble carboxylic acid, water and unreacted hydrogen peroxide; the solvent system of substantially purely organic percarboxylic acid solutions (i.e., percarboxylic acid solutions which have a low water content or are substantially anhydrous) contains one or more organic solvents and optionally unreacted carboxylic acid.

Preferred aqueous equilibrium percarboxylic acid solutions contain the percarboxylic acid, the carboxylic acid on which it is based, hydrogen peroxide and water at equilibrium. A particularly preferred percarboxylic acid solution substantially consists of 2.5 to 43 wt. % of peracetic acid, 5 to 74 wt. % of acetic acid, 1 to 50 wt. % of hydrogen peroxide, 10 to 60 wt. % of water and 0.5 to 10 wt. % of polyphosphoric acid together with 0 to 0.5 wt. % of one or more conventional stabilizers.

The stability of percarboxylic acid solutions according to the invention may be further increased by the presence of one or more conventional stabilizers. Stabilizer concentration is generally below 0.1 wt. % relative to the solution (below 1000 ppm). Suitable compounds which may be considered as stabilizers are those from the series of (a) chelating agents based on phosphonic acids, such as hydroxy- and aminophosphonic acids, amino- and hydroxycarboxylic acids, N-heterocyclic carboxylic acids together with salts of the stated acids, (b) pyrophosphoric acid and the salts thereof, (c) free radical scavengers based on alkylated hydroxyaromatics, and (d) tin compounds. Such compounds are well known in the art.

Examples of those phosphonic acids which form chelate complexes with divalent metals which may be mentioned are: phosphonosuccinic acid, 2-phosphonobutane-1,2,4-tricarboxylic acid; examples of hydroxyphosphonic acids are 1-hydroxyethane-1,1-diphosphonic acid and the homologues with 3 to 6 C atoms; examples of aminophosphonic acids are aminotrimethylenephosphonic acid, dimethylaminomethane-diphosphonic acid, 1-amino-1-phenylmethanediphosphonic acid, aminoacetic acid/N,N-di (methylenephosphonic acid), ethylenediaminetetra (methylenephosphonic acid), hexamethylenediaminetetra (methylenephosphonic acid), diethylenetriaminepenta (methylenephosphonic acid), 3-amino-propane-1-hydroxy-1,1-diphosphonic acid. Aminocarboxylic acid based chelating agents which may be cited are aminotriacetic acid and ethylenediaminetetraacetic acid; hydroxycarboxylic acids which may be mentioned are citric acid and poly-$\alpha$-hydroxyacrylic acid; N-heterocyclic carboxylic acids which may be mentioned are picolinic acid, dipicolinic acid, quinolinic acid, 2,4-lutidinic acid, dinicotinic acid, together with the alkali metal and ammonium salts of the compounds within group (a). The tin stabilizers are preferably hydrates of stannates of the formula Me2SnO3, in which Me represents alkali metal or ammonium; in order to avoid turbidity effects, stannates are used only in very small quantities, conventionally of below 200 ppm, calculated as Sn. The above compounds are well known in the art. Aqueous equilibrium percarboxylic acid solutions with particularly good storage stability and corrosion resistance with regard to stainless steel have solutions containing dipicolinic acid as an additional stabilizer.

Production of a percarboxylic acid solution according to the invention comprises reacting a carboxylic acid having 1 to 12 C atoms and one or two carboxyl groups with hydrogen peroxide in the presence of a solvent system and an acidic catalyst at 0° to 70° C., which is characterized in that the catalyst used is a polyphosphoric acid of the formula $H_{n+2}P_nO_{3n+1}$, in which n denotes the average degree of condensation which is greater than or equal to 2.3, in a quantity of 0.2 to 10 wt. % relative to the percarboxylic acid solution.

The polyphosphoric acid catalyst according to the invention surprisingly exhibits substantially higher catalytic activity than phosphoric acid, pyrophosphoric acid and metaphosphoric acid ($H_3P_3O_9$), such that equilibrium is substantially more rapidly established than with the above-stated phosphoric acids. In the process according to the present invention, a polyphosphoric acid is used which has an average (=mean) degree of condensation n of greater than or equal to 2.3, preferably greater than 3 and in particular greater than 4. A polyphosphoric acid where n=2.3 contains, for example, 80.8 wt. % of $P_2O_3$, one where n=3 contains 82.5 wt. % of $P_2O_3$; conventional commercial polyphosphoric acid having a $P_2O_5$ content of around 85 wt. % is highly suitable as a catalyst for the process according to the present invention. The polyphosphoric acid is used in that quantity in which it is to be contained in the percarboxylic acid solution to be produced. In order to produce the preferred aqueous percarboxylic acid solutions, a sufficiently water soluble carboxylic acid is mixed with an aqueous hydrogen peroxide solution and reacted in the presence of the polyphosphoric acid catalyst according to the invention; the reaction conveniently proceeds until an equilibrium is established and the resultant reaction mixture contains, in addition to the percarboxylic acid, unreacted carboxylic acid, water, and unreacted hydrogen peroxide together with polyphosphoric acid. The reaction proceeds at between 0° and 70° C., but a temperature of 10° to 30° C. is preferred.

Hydrogen peroxide is conventionally used in the reaction in the form of an aqueous hydrogen peroxide solution; the $H_2O_2$ content of such solutions is usually between 5 and 85 wt. %, preferably between 30 and 70 wt. %.

Where necessary with regard to the desired percarboxylic acid concentration, water may additionally be added to the reaction system as a component of the solvent system. When reacting moderately water soluble carboxylic acids and percarboxylic acids, alcohols may additionally be used as solubilizing agents, wherein it must, however, be noted that in this case the equilibrium system additionally contains the corresponding carboxylic acid esters and percarboxylic acid esters.

When producing low-water or anhydrous solutions containing longer-chain or aromatic percarboxylic acids, it is convenient to react the carboxylic acid in the presence of a suitable oxidation-resistant organic solvent or solvent system with aqueous hydrogen peroxide in the presence of the polyphosphoric acid catalyst and to shift the equilibrium towards the desired side, for example by azeotropic distillation of water.

The polyphosphoric acid catalyst may be added either to the carboxylic acid to be reacted or to the aqueous hydrogen peroxide before the reaction; self-evidently, it is also possible to add the catalyst to the mixture of carboxylic acid and aqueous hydrogen peroxide. Where the percarboxylic acid solution is additionally intended to contain one or more stabilizers, these are added either to one or both of the reactants before the reaction or to the reaction mixture during or after the reaction.

In order to produce aqueous equilibrium percarboxylic acid solutions, such as an aqueous peracetic acid or perpropionic acid solution, a carboxylic acid and an aqueous hydrogen peroxide solution are reacted in such a quantity that a percarboxylic acid solution containing 5 to 15 wt. % of percarboxylic acid is preferably produced; depending upon the selected molar ratio of carboxylic acid to $H_2O_2$ to water, it is possible to produce solutions which differ with regard to their $H_2O_2$ concentration at a constant percarboxylic acid concentration.

It has been surprisingly found that percarboxylic acid solutions may be stored, transported and handled in conventional stainless steel containers if the percarboxylic acid contains polyphosphoric acid in a concentration of 0.2 to 10 wt. %. Such solutions also do not give rise to corrosion of the container material.

The percarboxylic acid solutions according to the present invention are distinguished in that the catalyst used for the production thereof is simultaneously a stabilizer and corrosion inhibitor. Production of the percarboxylic acid solutions requires no measures other than those known in the prior art, with the exception of the use of the polyphosphoric acids necessary according to the invention instead of the hitherto conventional mineral acids as catalyst. By using polyphosphoric acid as a combined catalyst/stabilizer, corrosion inhibitors and optionally additionally one or more known stabilizers, it is surprisingly possible to obtain percarboxylic-acid solutions which still pass the "at least 60° C." SADT test after contact with stainless steel (self accelerated decomposition test; UN guidelines relating to UN class 5.2; see Orange Book/Transport of Dangerous Goods; Tests and Criteria, part II, section 4, 1990, pages 205–209), so satisfying the preconditions for a transport authorization for percarboxylic acid solutions in stainless steel containers.

The invention is further illustrated in the following examples:

EXAMPLES 1–5 (COMPARATIVE) AND EXAMPLE 6 (ACCORDING TO THE INVENTION):

Time to establish equilibrium during production of a 5 wt. % aqueous peracetic acid using 1 wt. % of various catalysts, relative to the reaction mixture.

A mixture prepared from 275 g of 50 wt. % hydrogen peroxide, 60 g of acetic acid, 160 g of completely deionised water and 5 g of catalyst was maintained at 20° C. and the increase in peracetic acid content monitored over time by redox titration, until the peracetic acid content remained constant, i.e. until equilibrium had been reached. To this end, samples were taken, the hydrogen peroxide contained therein reacted by rapid titration with Ce(IV) sulphate and ferroin indicator, the sample was immediately thereafter combined with an excess of potassium iodide and the iodine liberated by reaction with peracetic acid was titrated with thiosulfate and starch indicator.

The increase in peracetic acid concentration was evaluated in accordance with first-order reaction kinetics. To this end, $\ln[(c_G-c)/c_G]$ was plotted against reaction time t, wherein $c_G$ is the peracetic acid concentration at equilibrium and c the peracetic acid concentration at time t. Plotting the values produces a straight line, from the gradient of which were calculated the times shown in table 1 taken to achieve 88% of the equilibrium concentration.

TABLE 1

| Example | Catalyst | Time to achieve 88% of the peracetic acid equilibrium concentration |
|---|---|---|
| 1 | $H_2SO_4$ | 24 h |
| 2 | $HNO_3$ | 40 h |
| 3 | $H_3PO_4$ | 125 h |
| 4 | $H_4P_2O_7$ | 83 h |
| 5 | meta-$H_3P_3O_9$ | 263 h |
| 6 | polyphosphoric acid | 47 h |

Example 6 (according to the invention) shows, in comparison with examples 1 to 5 (=not according to the invention) that polyphosphoric acid exhibits unexpectedly high catalytic activity with regard to establishing the equilibrium between peracetic acid, acetic acid, hydrogen peroxide and water, which is equivalent to the activity of the strong mineral acid nitric acid (example 2). The action of polyphosphoric acid is distinctly higher than the action of ortho-phosphoric acid (example 3), meta-phosphoric acid (example 5) and pyrophosphoric acid (example 4).

The peracetic acid mixtures produced according to the invention thus have the advantage over the peracetic acid mixtures containing pyrophosphoric acid disclosed in JP 4 243 861 that they may be produced more rapidly under the same reaction conditions or with smaller quantities of mineral acid and thus more economically. Polyphosphoric acid is moreover distinctly cheaper than pyrophosphoric acid.

EXAMPLES 7 TO 11

Decomposition of 5 wt. % aqueous peracetic acid by contact with V2A steel

A mixture prepared from 550 g of 50 wt. % $H_2O_2$, 120 g of acetic acid, 320 g of completely deionised water and 0.5 g of dipicolinic acid was mixed with the quantity of mineral acid shown in table 2 as catalyst and left to stand until equilibrium was established. A sheet of V2A stainless steel with a surface area of 150 $cm^2$ was immersed in this equilibrium mixture and the mixture stirred for 13 days at 20° C. A 100 ml portion of each mixture was then heated to 60° C. and the quantity of gas formed by decomposition of the peracetic acid was determined volumetrically. Table 2 summarizes the results.

TABLE 2

| Example | Added mineral acid in wt. % | Quantity of gas formed by peracetic acid decomposition in ml/h |
|---|---|---|
| 7 | 1% $H_2SO_4$ | 14 |
| 8 | 2% $H_2SO_4$ | 40 |
| 9 | 1% $H_2SO_4$ + 1% $H_3PO_4$ | 2.8 |
| 10 | 1% polyphosphoric acid | 0.4 |
| 11 | 2% polyphosphoric acid | 0.4 |

After prolonged contact with stainless steel, the peracetic acid solutions according to the invention (examples 10 and 11) thus surprisingly exhibit the same rates of decomposition as solutions which have never come into contact with stainless steel. In comparison tests without contact with stainless steel, decomposition rates of 0.4 to 0.8 ml/h were found under the same conditions for the peracetic acid solutions from examples 7 to 11.

Further variations and modifications of the foregoing will be apparent to those skilled in the art and such variations and modifications are intended to be encompassed by the claims that are appended hereto.

German Priority Application 195 17 465.8 filed on 12 May 1995 is relied on and incorporated by reference in its entirety.

We claim:

1. A process for the production of a percarboxylic acid solution containing a percarboxylic acid having 1 to 12 C atoms and one or two peroxycarboxyl groups and a solvent system, and a polyphosphoric acid of the formula $H_{n+2}P_nO_{3n+1}$ comprising reacting a carboxylic acid having 1 to 12 C atoms and one or two carboxyl groups with hydrogen peroxide in the presence of said solvent system and an acidic catalyst at a temperature of 0° to 70° C. to produce a reaction mixture containing said percarboxylic acid; wherein said catalyst in said polyphosphoric acid of the formula $H_{n+2}P_nO_{3n+1}$, in which n denotes the average degree of condensation and is greater than or equal to 2.3, in a quantity of 0.2 to 10 wt.% relative to said percarboxylic acid solution.

2. The process according to claim 1, wherein said quantity of said polyphosphoric acid is 0.5 to 5 wt. %.

3. The process according to claim 2, wherein said quantity of said polyphosphoric acid is 1 to 3 wt. %.

4. The process according to claim 1, wherein n is greater than 3.

5. The process according to claim 4, wherein n is greater than 4.

6. The process according to claim 1, wherein n=2.3 and said polyphosphoric acid contains 80.8 wt. % of $P_2O_5$.

7. The process according to claim 1, wherein n=3 and said polyphosphoric acid contains 82.5 wt.% of $P_2O_5$.

8. The process according to claim 1, wherein said polyphosphoric acid contains about 85 wt. % of $P_2O_5$.

9. The process according to claim 1, wherein said percarboxylic acid solution is an aqueous percarboxylic acid solution and said reaction mixture contains said aqueous percarboxylic acid, unreacted carboxylic acid, water, and unreacted hydrogen peroxide together with polyphosphoric acid.

10. The process according to claim 9, wherein said temperature is 10° to 30° C.

11. The process according to claim 1, wherein said hydrogen peroxide is an aqueous hydrogen peroxide solution containing 5 to 85 wt. % $H_2O_2$.

12. The process according to claim 11, wherein said hydrogen peroxide is an aqueous hydrogen peroxide solution containing 30 to 70 wt. % $H_2O_2$.

13. The process according to claim 11, wherein said solvent system is aqueous and contains no organic solvents other than the carboxylic acid on which said percarboxylic acid is based.

14. The process according to claim 1, comprising reacting an aliphatic monocarboxylic acid having 1 to 6 C atoms or an α,ω-dicarboxylic acid having 4 to 6 C atoms with an aqueous hydrogen peroxide solution until equilibrium is established.

15. The process according to claim to 1, further comprising adding at least one stabilizer in a total quantity of up to 0.1 wt. %.

16. A percarboxylic acid solution with improved stability when in contact with stainless steel, consisting essentially of a percarboxylic acid having 1 to 12 C atoms and one or two peroxycarboxyl groups and a solvent system, wherein said percarboxylic acid solution contains at least one polyphosphoric acid of the formula $H_{n+2}P_nO_{3n+1}$, in which n denotes the average degree of condensation and is greater than or equal to 2.3, in a quantity of 0.2 to 10 wt. % relative to said percarboxylic acid solution; said percarboxylic acid solution produced by a process reacting a carboxylic acid having 1 to 12 C atoms and one or two carboxyl groups with hydrogen peroxide in the presence of a solvent system, an acidic catalyst and optionally at least one stabilizer, at a temperature 0° to 70° C. to produce a reaction mixture containing said percarboxylic acid; wherein said catalyst is a polyphosphoric acid of the formula $H_{n+2}P_nO_{3n+1}$, in which n denotes the average degree of condensation and is greater than or equal to 2.3, in a quantity of 0.2 to 10 wt. % relative to said percarboxylic acid solution.

17. The percarboxylic acid solution according to claim 16, wherein said percarboxylic acid solution contains 2.5 to 43 wt. % of peracetic acid, 5 to 74 wt. % of acetic acid, 1 to 50 wt. % of hydrogen peroxide, 10 to 60 wt. % of water and 0.5 to 10 wt. % of polyphosphoric acid together with 0 to 0.5 wt. % of at least one stabilizer.

18. A process for the storage of a percarboxylic acid solution in a stainless steel container with reduced risk of decomposition of said percarboxylic acid, comprising storing the percarboxylic acid according to claim 1 in a stainless steel container; wherein said reduced risk is in comparison to a percarboxylic acid solution which does not contain at least one polyphosphoric acid of the formula $H_{n+2}P_nO_{3n+1}$.

in which n denotes the average degree of condensation and is greater than or equal to 2.3.

19. The process according to claim 1, said process comprising adding said catalyst to said carboxylic acid or to said hydrogen peroxide or to a mixture of said carboxylic acid and said hydrogen peroxide.

* * * * *